(12) United States Patent
Halbritter et al.

(10) Patent No.: US 6,423,861 B1
(45) Date of Patent: Jul. 23, 2002

(54) METHOD OF PRODUCING DIMETHYL SULFITE

(75) Inventors: Klaus Halbritter, Heidelberg; Hans-Josef Sterzel, Dannstadt-Schauernheim; Christian Tragut, Wachenheim; Eva Freudenthaler, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/889,580

(22) PCT Filed: Feb. 1, 2000

(86) PCT No.: PCT/EP00/00771

§ 371 (c)(1),
(2), (4) Date: Jul. 31, 2001

(87) PCT Pub. No.: WO00/46218

PCT Pub. Date: Aug. 10, 2000

(51) Int. Cl.[7] .............................................. C07C 301/00
(52) U.S. Cl. ...................................................... 558/59
(58) Field of Search ...................................... 558/60, 59

(56) References Cited

U.S. PATENT DOCUMENTS 3,428,734 A * 2/1969 von Schmeling et al.
4,555,522 A 11/1985 Martin

OTHER PUBLICATIONS

CA:86:89238 abs of J Org. Chem. by Wilson et al 4294) pp 765–766.*
H. F. Van Woerden, Chemical Reviews, vol. 93, pp. 557–571, "Organic Sulfites," 1963.
R. Riemschneider, et al., Zeitschrift Fuer Naturforschung, vol. 15B, pp. 552–554, "Buten(2)-Diol-1,4-Cycl. Sulfit," 1960.
B. Voss, et al., Justus Liebigs Ann. Chem., vol. 485, pp. 275, "Beilstein Institur Fuer Literatur Der Organischen Chemie," Reaction ID 178517, 1931 (Abstract only).
R. J. Olsen, et al., J. Org. Chem., vol. 48, No. 21, pp. 3847–3848, Reaction ID 1581878, "Beilstein Institut Fuer Literatur Der Organischen Chemie," 1983, (Abstract only).
J. March, J. Wiley, pp. 397–398, "Organic Chemistry, Reactions, Mechanisms, and Structure," 1992.
B. Voss, et al., vol. 485, pp. 260–261 and 274–275, "Ueber Die Ester Der Schwefligen Saeure, I", "Beilstein Institut Fuer Literatur Der Organischen Chemie," 1931.

* cited by examiner

Primary Examiner—Jean F. Vollano
(74) Attorney, Agent, or Firm—Oblon, Spivak, McClelland, Maier & Neustadt, P.C.

(57) ABSTRACT

Dimethyl sulfite is prepared by transesterification of a cyclic alkylene sulfite of at least 2 carbon atoms with methanol, in the presence or absence of a catalyst, by a process which is carried out continuously in a column.

8 Claims, 1 Drawing Sheet

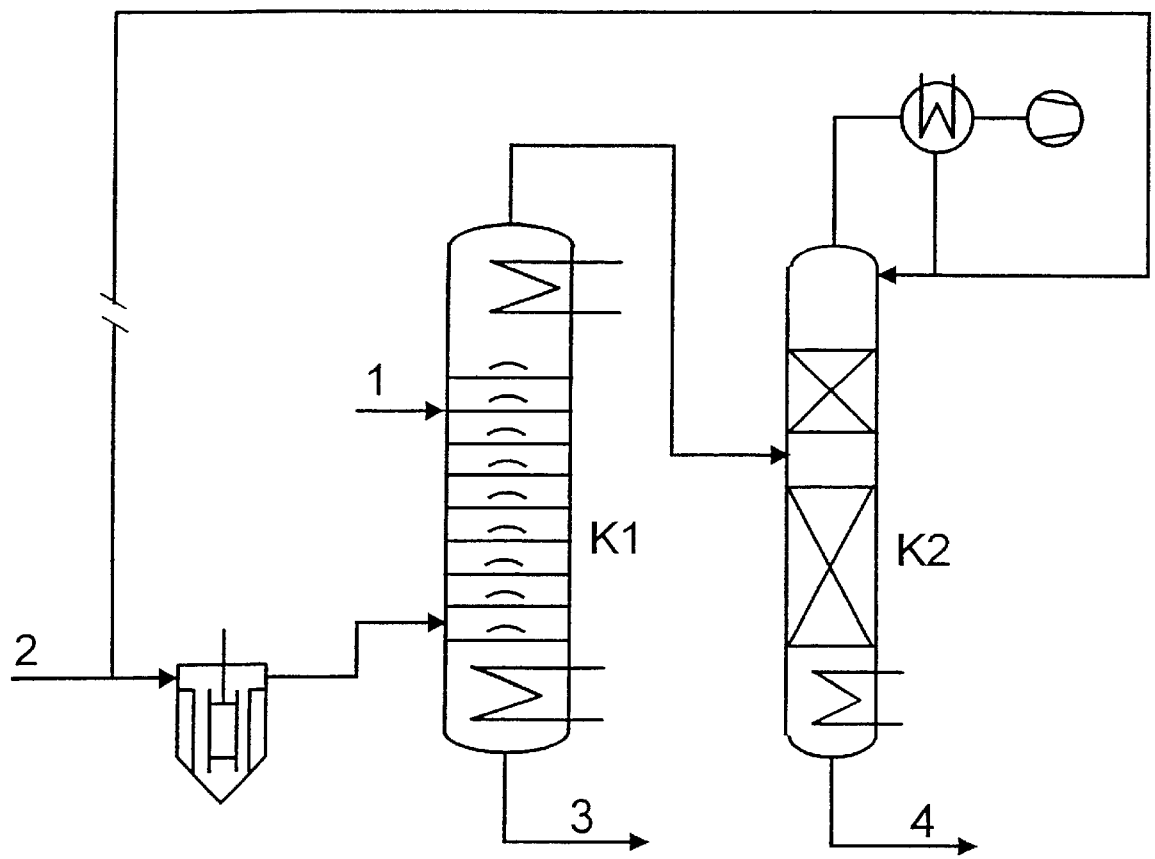

METHOD OF PRODUCING DIMETHYL SULFITE

This application is the natural phase of PCT/EP00/00771, filed Feb. 1, 2000, now WO00/46218.

The present invention relates to a process for the preparation of dimethyl sulfite from a higher dialkyl sulfite or a cyclic alkylene sulfite and methanol.

A conventional process for the preparation of dialkyl sulfites, in particular of dimethyl sulfite, is the reaction of thionyl chloride with an alcohol, in the case of dimethyl sulfite, with methanol. The preparation of dimethyl sulfite by such a reaction is described, for example, in W. Voss et al., Justus Liebigs Ann. Chem. 485 (1931), 258–283.

However, the reaction with thionyl chloride has the disadvantage that large amounts of hydrogen chloride are formed in the reaction, which means that the materials used have to meet particular requirements with regard to corrosion. If the hydrogen chloride is not removed sufficiently rapidly from the reaction mixture, it undergoes a secondary reaction with the dialkyl sulfite formed to give alkyl chloride, alcohol and sulfur dioxide.

It is also known that dialkyl sulfites and cyclic alkylene sulfites can undergo with alcohols transesterification reactions in which transesterified alkyl sulfites corresponding to the alcohols used are formed. This transesterification reaction is an equilibrium reaction. It is catalyzed by acids and bases but takes place at elevated temperatures even without a catalyst.

R. Riemschneider et al., Z. Naturforschung 15 b (1960), 552–554, describe the preparation of a cyclic sulfite, of 2-butene-1,4-diol, by reacting dimethyl sulfite with the corresponding diol. To shift the equilibrium of the reaction toward the desired product, methanol formed is removed continuously by distillation.

H. F. van Woerden, Chem. Rev. 93 (1963), 557–571, describes the transesterification of dimethyl sulfite with ethylene glycol to give ethylene sulfite and methanol without a catalyst. To obtain ethylene sulfite in good yields the methanol formed is removed continuously to shift the resulting equilibrium toward the product.

Such a procedure is possible only when the alcohol forming has a lower boiling point than the alcohol used.

In the preparation of dimethyl sulfite by reacting cyclic alkylene sulfites, the alcohol used is methanol. The alcohol forming therefore always has a higher boiling point than the methanol used. In the case of an equilibrium shift by means of distillation, as described in the literature, the methanol would first be removed and thus the reverse reaction to the starting materials would be promoted, instead of the shift of equilibrium toward the product.

It is an object of the present invention to provide a process for the preparation of dimethyl sulfite—starting from cyclic alkylene sulfites—in which dimethyl sulfite can be obtained in good yields and in high purity.

We have found that this object is achieved by a process for the preparation of dimethyl sulfite by transesterification of a cyclic alkylene sulfite of at least 2 carbon atoms with methanol, in the presence or absence of a catalyst. The novel process is carried out continuously in a column.

The novel process has the advantage that hydrogen chloride which can attack the materials used and can react with the product formed is not formed, in contrast to the reaction of thionyl chloride with alcohols. The resulting alcohol can be further used for various applications.

The novel process is preferably carried out by the countercurrent method, methanol being added in the lower part of the column and flowing countercurrent to cyclic alkylene sulfite added in the upper part of the column.

The higher alcohol liberated and corresponding in the transesterification to the cyclic alkylene sulfite used is taken off continuously via the bottom of the column, and the resulting dimethyl sulfite is taken off continuously, together with unconverted methanol, via the top of the column.

The cyclic alkylene sulfite is referred to below as starting sulfite.

The alcohols liberated are diols.

The column in which the transesterification is carried out may be either a tray column or a packed column. Preferably, the column is a tray column, for example a bubble tray column.

The starting sulfite is generally metered in as a liquid in the upper part of the column.

The novel process is preferably carried out in the presence of a catalyst in order to accelerate the transesterification. Said catalyst is particularly preferably soluble in the starting sulfite used. Consequently, the catalyst can be added to the starting sulfite used and introduced together with said sulfite into the column. A particularly preferred catalyst is methanesulfonic acid.

With a sufficient residence time on the trays of the column, a catalyst can be dispensed with.

For simple metering, the catalyst is dissolved in the starting sulfite. The methanol used for the transesterification is generally metered in as a vapor in the lower part of the column.

The starting sulfite and methanol are generally added to the column in a molar ratio of 1 to at least 2. Methanol is preferably used in a stoichiometric excess of 5–20:1, particularly preferably of 10:1. The unconverted methanol is then preferably recycled to the process.

Essentially the diol liberated from the corresponding starting sulfite after the transesterification is present in the bottom of the column. In addition, the bottom product may contain small amounts of condensates of the diol, and any catalyst used.

The dimethyl sulfite (reaction product) is obtained at the top of the column together with unconverted methanol, generally in gaseous form.

The dimethyl sulfite obtained is preferably separated in a second column from the simultaneously obtained methanol. The product stream, containing dimethyl sulfite and methanol, is transferred in liquid form or preferably in gaseous form to the second column. The second column may be a tray column or packed column.

The second column is generally operated at a top pressure of from 100 mbar to 5 bar, preferably from 500 to 1000 mbar, particularly preferably at 800 mbar.

The bottom temperature in the second column at 800 mbar is from 100 to 110° C. and the reflux ratio is adjusted so that the top temperature is from 55 to 60° C.

Methanol is obtained at the top of the second column and is preferably recycled to the first column. The methanol is preferably recycled in vapor form in order to save energy. The first and the second columns are preferably connected to one another via feed lines.

In a particularly preferred embodiment, the novel process is carried out in a column system (see the FIGURE), comprising:

a first column (K1) in which the novel transesterification is carried out, and a second column (K2) in which the mixture of dimethyl sulfite and methanol, obtained at the top of the first column, is separated, wherein the first column has a feed for the starting sulfite and, if required, the catalyst (1), which leads into the upper part of the column, a feed for methanol (2), which leads into the lower part of the column, and an outlet for the diol, catalyst and any condensates of the diol (3) which are obtained in the bottom, and a connection from the top of the first column to the middle part of the second column is present, through which the mixture of dimethyl sulfite and methanol is fed to the second column, wherein the second column has an outlet for dimethyl sulfite (product) (4) obtained in the bottom, and a connection from the top of the second column to the lower part of the first column, through which the excess methanol obtained at the top of the second column can be recycled to the first column.

The metering of fresh methanol into the first column is preferably controlled by means of the temperature profile in the lower region of the second column. If the temperature in the lower region of the second column increases by too much, this means that there is insufficient methanol in the column system and the amount of methanol must be adjusted accordingly.

The preferably used cyclic alkylene sulfite is one of 2 to 6, particularly preferably 2 to 4, carbon atoms. Ethylene sulfite and propylene sulfite are very particularly preferably used.

While other cyclic alkylene sulfites which may be used as starting sulfite are obtainable essentially by reacting thionyl chloride and the corresponding alcohol, with the disadvantages mentioned at the outset, alkylene sulfites of the formula I

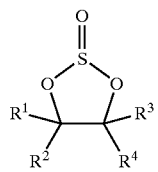

(I)

can be prepared, inter alia, starting from the corresponding epoxides II

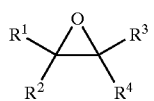

(II)

and sulfur dioxide by processes known from the literature. In the formulae I and II, $R^1$, $R^2$, $R^3$ and $R^4$, independently of one another, are each hydrogen, aryl or alkyl, preferably hydrogen or methyl. Ethylene sulfite and propylene sulfite are very particularly preferably used.

The diol formed in the novel reaction of alkylene sulfite and methanol can be used for other purposes after purification. For example, the ethylene glycol formed in the reaction of ethylene sulfite and methanol is widely used in industry, for example as a component for cooling liquids, a heat transfer medium, a hydraulic liquid or a solvent or as a starting material for further syntheses.

BRIEF DESCRIPTION OF THE DRAWINGS

In the attached drawing, the FIGURE shows a process diagram for carrying out the novel process. Therein:

K1: is a column for carrying out the transesterification

K2: is a column for separating methanol from a methanol/dimethyl sulfite mixture 1: denotes the starting sulfite (=higher dialkyl sulfite or cyclic alkylene sulfite) and catalyst, which may be dissolved in methanol 2: denotes methanol 3: denotes resulting (higher) alcohol or diol 4: denotes dimethyl sulfite The example which follows additionally illustrates the invention.

EXAMPLE

A stream of 100 g/h of ethylene sulfite and 0.44 g/h of methanesulfonic acid was fed in liquid form to the 40th tray of a bubble tray column (60 trays, 43 mm diameter) (stream 1). A stream of 400 g/h of methanol vapor was metered into the bottom of the column under temperature control. The major part of the methanol was recycled from the second column and supplemented with fresh methanol (60 g/h) under temperature control (stream 2). The bottom product of the column was heated to 192° C. and pumped out with level control (stream 3). It predominantly comprised ethylene glycol in addition to a little oligoethylene glycol and catalyst. The vapors of the column were cooled to 75° C. by means of a reflux condenser and fed into a second column (packed column, 43 mm diameter, 2 m laboratory fabric packing, 1000 cm$^2$/cm$^3$ surface area) This was operated at a top pressure of 800 mbar. The bottom product of the second column was heated to 105° C. It contained the dimethyl sulfite and was discharged with level control (stream 4). The reflux ratio was adjusted so that the temperature in the upper part of the column was 58° C.

We claim:

1. A process for the preparation of dimethyl sulfite by transesterification of a cyclic alkylene sulfite of at least 2 carbon atoms with methanol, in the presence or absence of a catalyst, wherein the process is carried out continuously in a column by the countercurrent method, in which methanol is added in the lower part of the column and flows countercurrent to cyclic alkylene sulfite added in the upper part of the column.

2. A process as claimed in claim 1, wherein a catalyst soluble in the cyclic alkylene sulfite is used.

3. A process as claimed in claim 2, wherein the catalyst used is methanesulfonic acid.

4. A process as claimed in claim 1, wherein the cyclic alkylene sulfite and methanol are added to the column in a ratio of 1 to at least 2.

5. A process as claimed in claim 1, wherein the dimethyl sulfite is separated in a second column from the unconverted methanol taken off together with the dimethyl sulfite via the top of the column.

6. A process as claimed in claim 5, wherein the first and the second columns are connected to one another via feed lines.

7. A process as claimed in claim 1, wherein the cyclic alkylene sulfite has 2 to 6 carbon atoms.

8. A process as claimed in claim 7, wherein the cyclic alkylene sulfite used is ethylene sulfite or propylene sulfite.

* * * * *